United States Patent
Giudicissi-Filho (10) Patent No.: US 9,556,225 B2
(45) Date of Patent: Jan. 31, 2017

(54) PEPTIDE STIMULATOR OF CELL SURVIVAL AND PROLIFERATION

(71) Applicant: União Química Farmacêutica Nacional S/A, São Paulo (BR)

(72) Inventor: Miguel Giudicissi-Filho, São Paulo (BR)

(73) Assignee: UNIAO QUIMICA FARMACEUTICA NACIONAL S/A, Sao Paulo, SP (BR)

(*) Notice: Subject to any disclaimer, the term of this patent is extended or adjusted under 35 U.S.C. 154(b) by 0 days.

(21) Appl. No.: 14/515,279

(22) Filed: Oct. 15, 2014

(65) Prior Publication Data

US 2016/0108086 A1    Apr. 21, 2016

(51) Int. Cl.
C07K 7/06    (2006.01)

(52) U.S. Cl.
CPC ..................................... *C07K 7/06* (2013.01)

(58) Field of Classification Search
None
See application file for complete search history.

(56) References Cited

U.S. PATENT DOCUMENTS

| 8,354,103 B2* | 1/2013 | Sleeman et al. ............ 424/130.1 |
| 2003/0215914 A1* | 11/2003 | Houtzager et al. .......... 435/69.1 |
| 2013/0330335 A1* | 12/2013 | Bremel et al. ............. 424/134.1 |

OTHER PUBLICATIONS

Betts et al., Bioinformatics for Geneticists, 2003, chapter 14, pp. 290-318.*
Flores et al., EMBL/GenBank/DDBJ databases, 2006, result 1.*
Calabria, Merck Manual, http://www.merckmanual.com/professional/pediatrics/endocrine-disorders, accessed May 31, 2016.*

* cited by examiner

*Primary Examiner* — James H Alstrum Acevedo
*Assistant Examiner* — Roy Teller
(74) *Attorney, Agent, or Firm* — B. Aaron Schulman, Esq.; Stites & Harbison, PLLC (57) ABSTRACT

The invention provides a novel peptide, and derivatives thereof, which is stable in aqueous solution and which stimulates proliferation and survival of endothelial cells and/or fibroblasts. The present peptide can be used at least to promote the S phase of the cell cycle, to stimulate production of extracellular matrix proteins, to reduce apoptosis, to inhibit production of reactive oxygen species and/or to reduce or prevent damage to cell integrity or morphology under stress conditions of serum deprivation.

19 Claims, 7 Drawing Sheets

```
                        SEQUENCE LISTING

<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: synthetic sequence

<400> SEQUENCE: 1

Lys Asp Gly Lys Asp
1               5

<210> SEQ ID NO 2
<211> LENGTH: 10
<212> TYPE: PRT
<213> ORGANISM: Artificial Sequence
<220> FEATURE:
<223> OTHER INFORMATION: synthetic sequence

<400> SEQUENCE: 2

Asp Tyr Phe Lys Asp Gly Lys Asp Val Asn
1               5                   10
```

PEPTIDE STIMULATOR OF CELL SURVIVAL AND PROLIFERATION

BACKGROUND

The present application is directed to peptides which can stimulate cell survival and proliferation, pharmaceutical and cosmetic compositions thereof, and methods for their use. More specifically, the peptides are active to stimulate the survival and proliferation of fibroblasts and/or endothelial cells.

The ability of organisms to repair or regenerate tissues is one of the most important features in nature and is a survival factor for life forms from bacteria to humans. The skin, the largest organ in humans, exhibits a complex mechanism of wound healing and regeneration. While "regeneration" describes the tissue-specific replacement of tissue such as superficial epidermis, mucosa or skin in response to natural fluctuation or damage, "repair", or wound healing, refers to non-specific healing of wounds involving scar formation and fibrosis.

In mature skin, wound repair usually begins with hemostatic and inflammatory processes, followed by a proliferative phase and epithelialization, angiogenesis and collagen production, and ends with the formation of a permanent scar. The discovery of new compounds that act on regeneration can provide information on how to accelerate wound healing, as well as how to improve the cosmetic aspects of healing.

Aging is a complex phenomenon characterized by progressive decline in physiological functions often accompanied by many pathological diseases. It is known that the loss of elasticity in the skin associated with chronological aging and wrinkling is associated with the increase of senescent fibroblasts. Fibroblasts have numerous functions, including cell-cell communication and signaling with other fibroblasts and endothelial cells, and the synthesis and deposition of extracellular matrix, the primary constituent in the structural assembly of the dermis, the deep layer of the skin. These cell-cell contacts affect electrophysiological properties, the secretion of growth factors and cytokines, and enhancement of blood vessel formation. Thus, fibroblasts play a critical role for maintaining the proper function of tissues as well as remodeling.

Senescent fibroblasts lose the ability to synthesize proteins, especially collagen, which is a major component of the extracellular matrix. Molecules of the extracellular matrix (ECM) promote cell adhesion, activate intracellular signaling pathways and modulate the activities of various growth factors and proteins. The loss of collagen occurs in chronological aging and from exposure to extrinsic factors such as ultraviolet radiation or tobacco smoke. Age-related changes observed in fibroblasts include changes in cell morphology and metabolism, decreased proliferative potential, loss of responsiveness to growth factors, decreased production of extracellular matrix proteins such as collagen type I and III, and over-expression of proteases involved in the degradation of extracellular matrix. These modifications tend to decrease the ability of the adaptive response and wound healing, and therefore increase the susceptibility to disease and death.

To ensure normal growth and cell proliferation, it is essential for cells to coordinate the signals arising from nutrients and growth factors as well as inhibitory signals resulting from stress or intracellular signaling. In fact, the interrelationship between cell death, cell survival and cell cycle has become the subject of intense research in recent years.

Apoptosis is a type of programmed cell death that occurs individually, not affecting neighboring structures. The control of cell death is a result of the balance between the expression of anti- and pro-apoptotic proteins in several cell types. Much evidence suggests that mitochondria are the main organelles involved in the processes of cell signaling and death. The mitochondria-dependent intrinsic apoptosis pathway is activated by several stimuli, including damage to DNA, decreased levels of growth factors, heat shock, ultraviolet radiation, gamma radiation, and chemotherapy drugs. DNA damage, especially of mitochondrial DNA, has an important impact on the process of aging.

Among the responses and cellular components involved in mitochondria-dependent intrinsic apoptosis are the production of reactive oxygen species (ROS), loss of cytoplasmic membrane integrity, changes in mitochondrial membrane potential, release of calcium by mitochondria and endoplasmic reticulum, expression and activation of protein caspases and activation of anti- or pro-apoptotic molecules or activation of mitogens. The signaling pathways activated by those agents culminate in the mitochondrial outer membrane permeabilization and the release of soluble apoptotic proteins from the mitochondria intermembrane space. When apoptosis is activated, cytochrome c is released from the mitochondria intermembrane space and can be used as a marker of apoptosis. Pro-apoptotic proteins such as Bax and Bak stimulate the release of this protein, however anti-apoptotic proteins such as Bcl-2 and Bcl-XL inhibit its release. The cytochrome c promotes the activation of pro-caspase 9 to caspase-9, which in turn activates other caspases, culminating in cell death by apoptosis. Activated caspases target specific proteins that maintain the cell structure, leading to cytoskeletal disruption and, consequently, loss of cellular integrity.

The mitochondrion is the major source of intracellular reactive oxygen species (ROS), which play a fundamental role in cellular signaling pathways, mainly in cell proliferation and apoptosis. The interaction of macromolecules with various ROS can impair the function of these organelles and directly influence cell viability and culminate in cell death. Therefore, mitochondria may also be the primary target for the damaging effects of ROS. Some theories speculate that cumulative damage to mitochondria and mitochondrial DNA (mtDNA) caused by ROS is one of the causes of aging. Moreover, extracellular matrix (ECM) components of the basement membrane are not efficiently produced or are degraded by metalloproteinases, causing the loss of cell-matrix adhesion and contributing to cell death by apoptosis.

Because of this, there is an estimated global economic impact of increasing the costs of treating patients with degenerative problems. The search for new compounds or compositions capable of stimulating cell survival, proliferation and activity of fibroblasts is of great interest in the pharmaceutical field for cosmetic treatment and/or prevention of pathologies associated with aging and loss of extracellular matrix.

SUMMARY

One aspect of the present invention provides a synthetic peptide comprising the amino acid sequence KDGKD (SEQ ID NO: 1) and derivatives thereof. In at least one embodiment, the peptide comprises the amino acid sequence DYFKDGKDVN (SEQ ID NO: 2). In at least one embodiment, the peptide consists of the amino acid sequence DYFKDGKDVN (SEQ ID NO: 2).

Another aspect of the present invention provides a pharmaceutical composition comprising a peptide as described herein and one or more pharmaceutically acceptable carriers.

Still another aspect of the present invention provides a cosmetic composition comprising a peptide as described herein and one or more cosmetically acceptable carriers.

In another aspect, the present invention provides the use of a peptide as described herein for stimulating proliferation or survival of a cell. In a further aspect, the present invention provides a method of stimulating proliferation or survival of a cell, the method comprising exposing the cell to a peptide as described herein.

In at least one embodiment, the cell is an endothelial cell or fibroblast. In at least one embodiment, the fibroblast is a dermal fibroblast. In at least one embodiment, the peptide stimulates the synthesis of DNA by promoting the S phase of the cell cycle. In at least one embodiment, the peptide stimulates the production of at least one extracellular matrix (ECM) protein. In at least one embodiment, the at least one ECM protein is one or more proteins selected from collagen, fibronectin, laminin, and vitronectin. In at least one embodiment, the peptide reduces the production of reactive oxygen species (ROS). In at least one embodiment, the peptide reduces apoptosis. In at least one embodiment, the peptide reduces or prevents damage to cell morphology and/or integrity under stress conditions of serum deprivation.

In another aspect, the present invention provides use of a peptide as described herein in the preparation of a medicament for the treatment or prevention of a condition associated with insufficient proliferation or survival of cells. Yet another aspect of the present invention provides a method of treating or preventing a condition associated with insufficient proliferation or survival of cells in a subject in need thereof, the method comprising administering a peptide as described herein, or a pharmaceutical composition thereof, to the subject. In at least one embodiment, the cells are endothelial cells or fibroblasts. In at least one embodiment, the fibroblasts are dermal fibroblasts. In at least one embodiment, the subject is a human patient.

In at least one embodiment, the condition is associated with insufficient production of at least one extracellular matrix (ECM) protein. In at least one embodiment, the at least one ECM protein is one or more proteins selected from collagen, fibronectin, laminin, and vitronectin. In at least one embodiment, the condition is associated with production of reactive oxygen species. In at least one embodiment, the condition is associated with apoptosis. In at least one embodiment, the condition is associated with tissue degeneration.

In a still further aspect, the present invention provides a method of reducing or preventing damage to morphology or integrity of a cell under stress conditions of serum deprivation, the method comprising exposing the cell to a peptide as described herein.

BRIEF DESCRIPTION OF THE DRAWINGS

Further features of the present invention will become apparent from the following written description and the accompanying figures, in which.

DETAILED DESCRIPTION

The present invention provides peptides comprising the sequence KDGKD (SEQ ID NO: 1), or Lys-Asp-Gly-Lys-Asp and its derivatives. In at least one embodiment, the peptides have an amino acid sequence comprising the amino acid sequence DYFKDGKDVN (SEQ ID NO: 2), or Asp-Tyr-Phe-Lys-Asp-Gly-Lys-Asp-Val-Asn. In at least one embodiment, a peptide according to the present invention has an amino acid sequence consisting of the amino acid sequence DYFKDGKDVN (SEQ ID NO: 2), hereafter referred to as LONO-Q.

The present peptides can be chemically synthesized by methods well known in the art, including but not limited to well known solid phase methodology using a 4-methylbenzhydrylamine hydrochloride (MBHA) resin. Other methods for chemically synthesizing the present peptides include but are not limited to those methods described in publications, such as Bodanszky, M. and A. Bodanszky, *The Practice of Peptide Synthesis*. 2nd ed. 1994, Heidelberg: Springer-Verlag and Jones, J., *The Chemical Synthesis of Peptides*. 1991, Oxford: Clarendon Press. The peptides can then be purified by known methods, including but not limited to reverse phase high performance liquid chromatography (RP-HPLC) using a linear gradient of trifluoroacetic acid (1%) in acetonitrile and water.

The peptides can also be biologically synthesized using recombinant DNA technology. For example, in at least one embodiment, an expression vector containing a nucleic acid sequence encoding a peptide as described herein can be expressed in a suitable expression system, as will be understood by the skilled person.

Peptide concentrations can be determined by amino acid analysis, as well understood in the art.

Peptide analogues comprising the sequence KDGKD (SEQ ID NO: 1) or DYFKDGKDVN (SEQ ID NO: 2) can be synthesized as described above and characterized as understood in the art. Such analogues can be assessed for biological activity using the methods described herein, including in the Examples. Therefore, the person skilled in the art would be readily able to prepare, evaluate and select peptide analogues comprising the sequence KDGKD (SEQ ID NO: 1) or DYFKDGKDVN (SEQ ID NO: 2) as suitable for use in the methods described herein.

In at least one embodiment, the present peptides show useful biological properties. More particularly, in vitro experiments with primary dermal fibroblast cells (FN1) and human vein endothelial cells from umbilical cords (HU-VECs), as described further below, indicate that at least one embodiment of the present peptide can promote cell proliferation and/or cell survival in serum-deprived cells at a dose that is not toxic for cells.

Fibroblasts are involved in the synthesis of the proteins of the extracellular matrix (ECM) of the dermis. ECM proteins include but are not limited to collagen, fibronectin, laminin and vitronectin. Collagen is implicated in the solidity of the dermis, and therefore in the firmness of the skin and/or mucous membranes. In at least one embodiment, the present peptides have been shown to stimulate the production of one or more ECM proteins, as described further below. Stimulation of production of ECM proteins can have beneficial results, including but not limited to stimulating regeneration of tissue due to the loss of ECM by disease (for example, in diseases such as asthma involving dysfunction of collagen or ECM components) or damage (for example, wounds, trauma, cosmetic defects, cartilage disease, photo or chronological aging, etc.).

Therefore, in at least one embodiment, the present peptides can have one or more of the following biological activities:
   stimulating the proliferation and/or the activity of cells, including but not limited to fibroblasts and endothelial cells;
   stimulating the S phase of the cell cycle, corresponding to DNA synthesis;
   stimulating the production of one or more extracellular matrix (ECM) molecules in cells;
   reducing tissue degeneration;
   reducing the loss of cell integrity and/or morphology;
   reducing the production of reactive oxygen species; and/or
   reducing cell death by apoptosis.

The present invention also provides a pharmaceutical composition comprising a pharmaceutically effective amount of a peptide as described herein and one or more pharmaceutically acceptable carriers. In at least one embodiment, the pharmaceutical composition is suitable for dermatological use. In at least one embodiment, the pharmaceutical composition can be topically applied to skin.

The present invention also provides a cosmetic composition comprising a cosmetically effective amount of a peptide as described herein and one or more cosmetically acceptable carriers. In at least one embodiment, the cosmetic composition is suitable for dermatological use. In at least one embodiment, the cosmetic composition can be topically applied to skin.

In at least one embodiment, the pharmaceutical or cosmetic composition comprises a concentration of the peptide in the nanomolar range. In at least one embodiment, the concentration of the peptide in the composition is from about 20 nmol/L (nM) to about 50 nmol/L (nM). In at least one embodiment, the concentration of the peptide in the composition is from about 25 ng/mL to about 50 ng/mL.

In at least one embodiment, pharmaceutical or cosmetic compositions comprising a peptide as described herein can be useful to treat or prevent one or more conditions associated with insufficient proliferation or survival of cells, including but not limited to endothelial cells or fibroblasts including but not limited to dermal fibroblasts. Such conditions include but are not limted to insufficient production of ECM proteins, including but not limited to collagen, fibronectin, laminin, and vitronectin; production of reactive oxygen species; tissue degeneration; or apoptosis. Such conditions include but are not limited to asthma, diseases involving dysfunction of collagen or ECM components, wounds, trauma, cosmetic defects, cartilage disease, photo-induced aging and chronological aging.

EXAMPLES

Other features of the present invention will become apparent from the following non-limiting examples which illustrate, by way of example, the principles of the invention.

Example 1

Stability Analysis by Circular Dichroism

Materials and Methods:
   Circular dichroism is an accepted technique that allows a quick estimation of secondary structures of peptides and changes in their secondary structures dependent on peptide concentration, pH and buffer (Greenfield, N.J., *Methods to estimate the conformation of proteins and polypeptides from circular dichroism data*. Anal Biochem, 1996. 235(1): p. 1-10).

Measurement of the structural integrity of the peptide was carried out using sodium phosphate buffer at various pH values (6.0, 6.4, 6.8, 7.0, 7.4, 8.0) containing 125 µg/ml of the peptide. Peptide solutions were incubated overnight at room temperature (25° C.). Analyses of circular dichroism (CD) were performed on a J-810 spectropolarimeter controlled by Spectra Manager™ software (JASCO), using cuvettes with optical path length of 0.1 cm (Biotechnology Center—Instituto Butantan). The CD spectra were recorded in the range 183-260 nm every 0.1 nm. The spectrum of each sample was subtracted from the spectrum of the buffer without peptide.

Physicochemical properties were determined by using free software (Peptide property calculator, Innovagen: http://www.innovagen.se/custom-peptide-synthesis/peptide-property-calculator/peptide-property-calculator.asp).

Results:

The synthetic peptide in powder form was kept in the dark at −20° C. Peptides containing aromatic amino acids are recommended to be stored in the dark. A concentrated peptide solution was prepared in sterile distilled water and kept as a stock solution at −20° C. Before each experiment, the required amount of peptide was dissolved in culture medium.

Physicochemical properties: Molecular weight (MW)=1266.43; Number of residues: 10; Extinction coefficient: 5690 $M^{-1}$ $cm^{-1}$; Isoelectric point: pH 10.2; Net charge at pH 7.0: 1; Solubility: good water solubility.

Figure 1:
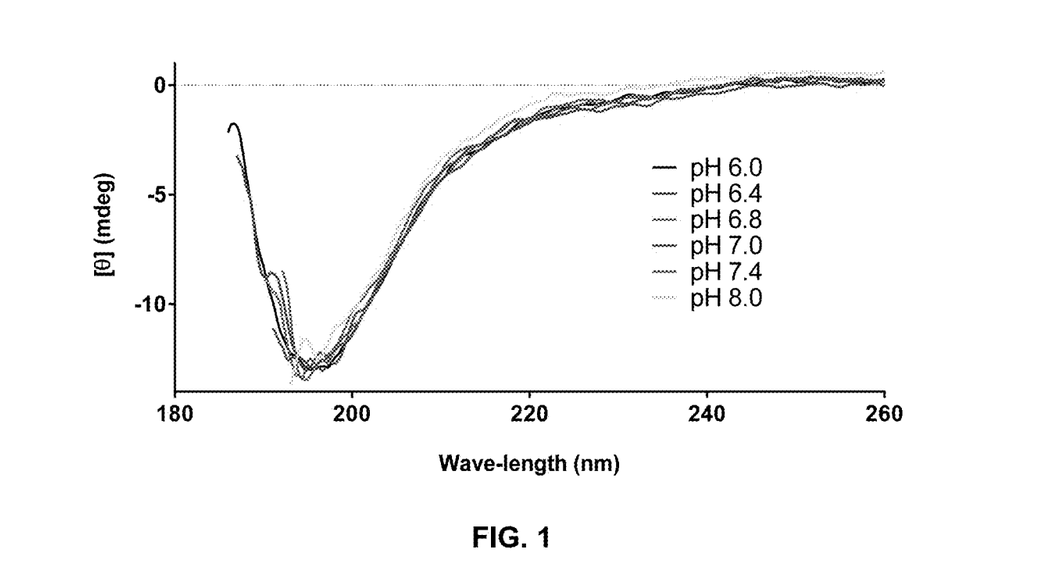
FIG. 1 is a line graph showing the circular dichroism (CD) spectra of the LONO-Q peptide (125 μg/ml) in sodium phosphate buffer at different pH values.

The peptide LONO-Q (125 μg/ml) was incubated at 25° C. in phosphate buffer with 100 mM sodium at different pH values for 24 hours. Analysis of circular dichroism demonstrates that the peptide LONO-Q remains stable at room temperature in phosphate buffer at all pH values tested (6.0 to 8.0) (FIG. 1). The CD spectra suggest that the peptide has similar secondary structure at all pH values tested.

Example 2

Cytotoxicity Assays and Cell Viability

Materials and Methods:

For in vitro cell culture tests, the peptide (previously dissolved in water and stored at −20° C.) was resuspended, at the desired concentration, in culture medium supplemented with fetal bovine serum (FBS). The concentration of FBS was selected depending on the requirements of each experiment.

The MTT method was used (Mosmann, T., *Rapid colorimetric assay for cellular growth and survival: application to proliferation and cytotoxicity assays*. J Immunol Methods, 1983. 65(1-2): p. 55-63). The viability test was performed in culture plates of 96 wells. Human umbilical vein endothelial cells (HUVEC, 1.5×$10^4$ cells/well) in RPMI (Roswell Park Memorial Institute) culture medium 1640 supplemented with 1% or 10% fetal bovine serum (FBS) were incubated in the absence or in the presence of different concentrations of the LONO-Q peptide (final volume of 200 μl). After 72 h, the supernatant was discarded and the cells washed twice with phosphate buffered saline (PBS) at pH 7.4 and incubated at 37° C. for 3 h with 100 μl of 0.5 mg/ml MTT reagent (3-(4,5-dimethylthiazol-2-yl)-2,5-diphenyl tetrazolium bromide) in PBS. The supernatant was removed and the reaction was stopped with 100 μl of dimethyl sulfoxide (DMSO). Absorbance values were determined at 540 nm using a SpectraMax™ 190 automatic plate reader (Molecular Devices, USA).

Figure 2:
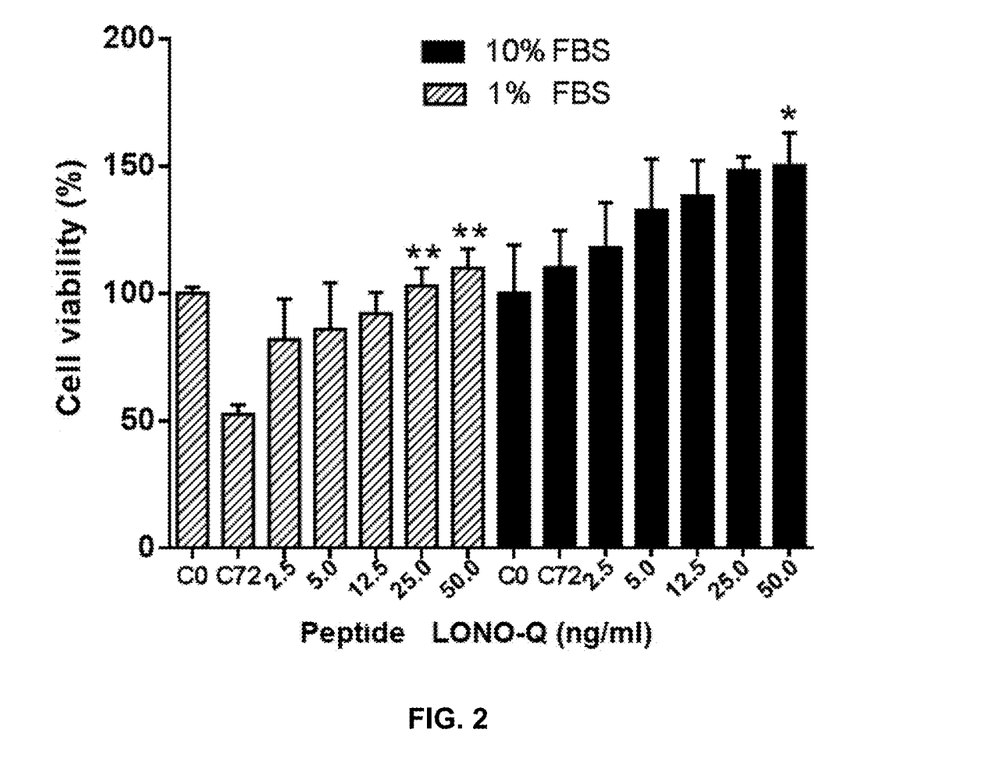
FIG. 2 is a bar graph showing the effect of LONO-Q peptide in a culture of endothelial cells (HUVECs) assessed by the MTT method. The cells were incubated for 72 hours in the presence or absence of the peptide in RPMI culture medium containing 1% or 10% of fetal bovine serum (FBS). C0=100% control cells was taken as time zero (before treatment); C72=control after 72 hours of treatment.

Results:

The effect of LONO-Q on cell viability of HUVECs subjected to serum deprivation (1% FBS) or normal growth medium (10% FBS) is shown in FIG. 2. The results were expressed as a percentage of cell viability relative to the untreated control at time zero (initial number of cells). Absorbance values were determined at 540 nm. The results were expressed as the average ±standard error of the mean (SEM) of 5 independent experiments. Statistical significance between the groups were determined by a one-way ANOVA test (*: p<0.05, **: p<0.01).

It was observed that after 72 h of treatment, the control containing 1% FBS lost approximately 50% of cells; this result validates this experiment. The addition of LONO-Q stimulated cell viability in a dose-dependent manner. Doses of 25 and 50 ng/ml gave statistically significant results (**: p<0.01) relative to the untreated control (1% FBS), being similar to control cells maintained in 10% FBS alone.

The addition of LONO-Q to fibroblasts under normal conditions (10% FBS) stimulated the cellular proliferation in a dose-dependent manner. The dose of 50 ng/ml LONO-Q gave statistically significant results (*: p<0.05).

Example 3

Analysis of Cell Proliferation of Human Dermal Fibroblasts

Materials and Methods:

Quantitative assessment of cell proliferation was performed by staining cells with carboxyfluorescein succinimidyl ester (CFDA-SE), as described previously (Asquith, B., et al., *Quantifying lymphocyte kinetics in vivo using carboxyfluorescein diacetate succinimidyl ester* (CFSE). Proc Biol Sci, 2006. 273(1590): p. 1165-71; Lyons, A. B., *Analysing cell division in vivo and in vitro using flow cytometric measurement of CFSE dye dilution*. J Immunol Methods, 2000. 243(1-2): p. 147-54). CFDA-SE is a lipophilic dye which reacts with amino groups of peptides and proteins, forming a stable amide linkage, which can be detected using flow cytometry analysis. The CFDA-SE passively diffuses into cells. It is colorless and nonfluorescent until its acetate groups are cleaved by intracellular esterases to produce a highly fluorescent, amine reactive succinimidyl ester of carboxyfluorescein, which is well conserved and can be fixed with aldehyde fixatives. The excess reagent and unconjugated by products passively diffuse into the extracellular environment where they can be washed away. When parent cells divide, CFDA-SE dye is equally distributed to the daughter cells, which therefore have half of the fluorescence intensity of the parents. The reduction of fluorescence intensity of cell generations in cell proliferation is easily detected by flow cytometry.

For the assay, human dermal fibroblasts (FN1) cells were seeded in six-well plates (1×$10^4$ cells/well), incubated with 5 mM CFDA—SE diluted in PBS, and cultured at 37° C. with 5% $CO_2$ for 15 minutes protected from light, according to the manufacturer's instructions (Vybrant® CFDA SE Cell Tracer Kit, MolecularProbes). Thereafter, FN1 cells were treated with 50 ng/ml of the LONO-Q peptide (diluted previously in culture medium) for 48 hours in the presence of 10% or 1% FBS . Subsequently, the cells were trypsinized and the cell buttons resuspended in 300 μl of FACS buffer with 2% paraformaldehyde and kept in the refrigerator until the moment of reading. Cell proliferation by CFDA—SE was estimated by the reduction in cell fluorescence. Fluorescence was determined for excitation at λ=492 nm and for emission at λ=517 nm (10000 events per sample) in a FACScalibur™ flow cytometry system (Becton and Dickson) using the CellQuest™ software. The parameters FSC (size) and SSC (granularity/complexity) was detected in linear scale and FL1-H on a logarithmic scale. Proliferation was analyzed using the program ModFit LT™ 2.0 (Verity Software House, Topsham, Me., USA). The figures are expressed as the average ±standard error of the mean (SEM) of 5 independent experiments (Student's t test).

Figure 3:
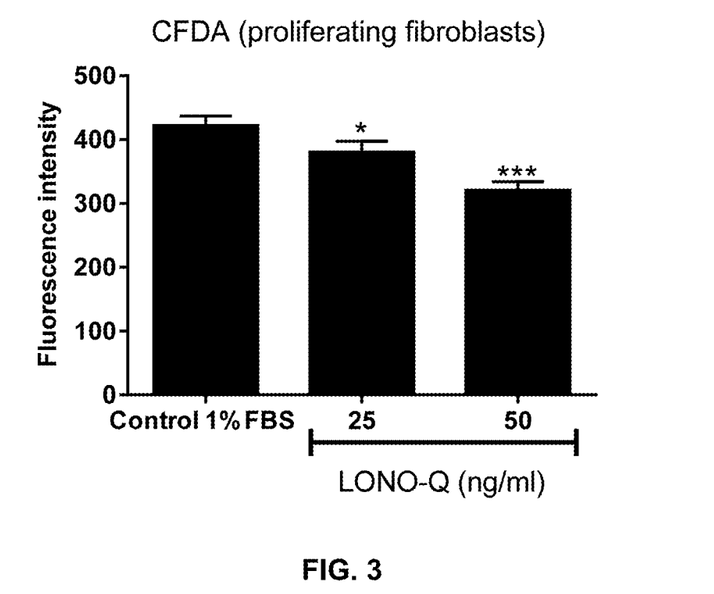
FIG. 3 is a bar graph showing the fluorescence intensity of proliferating fibroblasts (CDFA assay). FN1 fibroblasts cultured in 1% FBS were treated with 25 and 50 ng/ml LONO-Q for 48 hours in 1% FBS.
Figure 4:
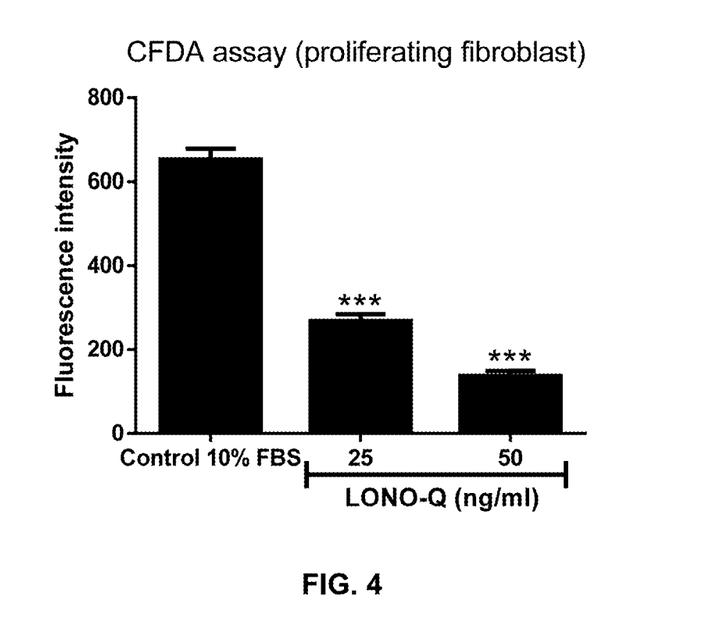
FIG. 4 is a bar graph showing the fluorescence intensity of proliferating fibroblasts (CDFA assay). FN1 fibroblasts cultured in 10% FBS were treated with 25 and 50 ng/ml LONO-Q for 48 hours in 10% FBS.

Results:

Carboxyfluorescein diacetate succinimidyl ester (CFDA-SE) is an amine-reactive, colorless, non-fluorescent dye that irreversibly couples to both intracellular and cell surface proteins (Hodgkin, P. D., J. H. Lee, and A. B. Lyons, *B cell differentiation and isotype switching is related to division cycle number*. J Exp Med, 1996. 184(1): p. 277-81). The intensity of fluorescence is inversely proportional to proliferation. In starvation conditions (1% FBS), the CFDA-SE staining showed that the treatment of FN1 cells with 25 and 50 ng/ml of LONO-Q induces a significant cytoprotection ($p<0.05$ and $p<0.001$, respectively, versus control 1% FBS), allowing the cells to proliferate even in serum deprivation conditions (FIG. 3). We then tested the effect of LONO-Q on FN1 cells treated in the presence of 10% FBS during 48 h. LONO-Q caused a more evident and statistically significant increase in the proliferation rate (FIG. 4) in cells treated with 25 and 50 ng/ml of peptide ($p<0.001$ versus control 10% FBS).

Example 4

Analysis of Cell Cycle Phases by Flow Cytometry

Materials and Methods:

The distribution of cells in the various cell cycle phases was determined by the content or amount of propidium iodide (PI) incorporated into the cell, measured by flow cytometry (Vindelov, L. L., I. J. Christensen, and N. I. Nissen, *Standardization of high-resolution flow cytometric DNA analysis by the simultaneous use of chicken and trout red blood cells as internal reference standards*. Cytometry, 1983. 3(5): p. 328-31). FN1 fibroblasts ($1\times10^6$ cells/ml, 6-well plate) were treated with 25 or 50 ng/ml LONO-Q for 48 hours in Dulbecco's Modified Eagle medium (DMEM) containing 1% or 10% FBS. After treatment, the FN1 cell suspensions were resuspended in 70% ethanol and kept in a freezer at $-20°$ C. for subsequent analysis of cell cycle phases. At the time of the experiment, cells were incubated in a PBS solution: 950 µl of PBS, 40 µl of PI (1 mg/ml) and 10 µl of Rnase: (10 mg/ml), to assess the quantity and integrity of DNA in the cell cycle phases. The results obtained by the acquisition program CellQuest™ acquired on a FACScalibur™ flow cytometer (Becton and Dickson, USA) were analyzed by FACS ModFit™ 2.8. The DNA content was expressed as mean percentage±standard error of the mean (SEM) of 3 independent experiments (Student's t test) of cells distributed in the different cell cycle phases: apoptotic cells, G0/G1, S and G2/M.

Figure 5:
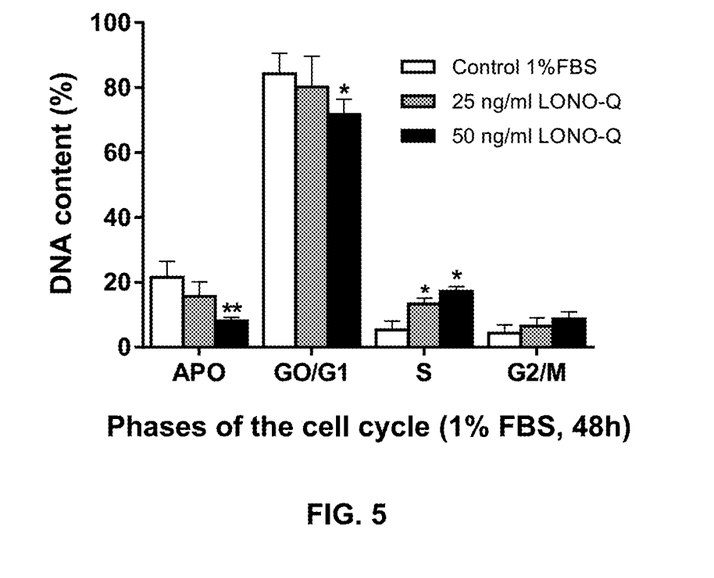
FIG. 5 is a bar graph showing the effect of peptide LONO-Q in the cell cycle of HUVECs incubated in RPMI medium containing 1% FBS. APO: apoptotic cells; G0/G1: cells in the quiescent state; S: S phase of DNA replication, G2/M phase: mitosis or cell division.
Figure 6:
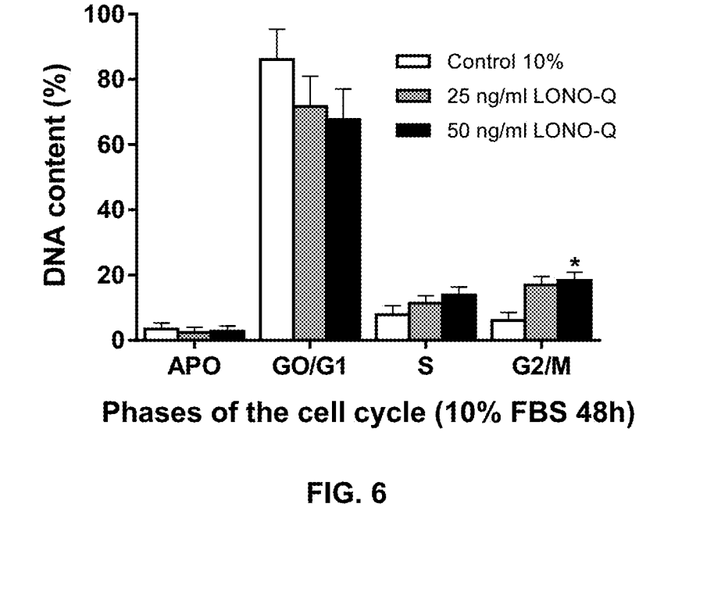
FIG. 6 is a bar graph showing the effect of peptide LONO-Q in the cell cycle of HUVECs incubated in RPMI medium containing 10% FBS. APO: apoptotic cells; G0/G1: cells in the quiescent state; S: S phase of DNA replication, G2/M phase: mitosis or cell division.

Results:

LONO-Q-induced cell survival was also studied by the analysis of the DNA content by FACS (FIGS. 5 and 6). In serum starvation conditions (1% FBS) (FIG. 5), LONO-Q caused an apparent dose-dependent increase of the S phase of the cell cycle, being statistically significant at concentration of 50 ng/ml ($5.4\pm2.7$% for control, and $17.2\pm1.5$*% for LONO-Q, n=3, *$p<0.05$ vs. control 1% FBS) and a statistically significant reduction of cells with fragmented DNA ($21.5\pm4.9$% of apoptotic cells, for control, and $8.1\pm1.1$% of apoptotic cells, for 50 ng/ml LONO-Q, respectively, n=3, $p<0.01$ vs. control 1% FBS). In normal conditions (10% FBS), a significant, cell cycle activation and proliferation was observed only in FN1 cells treated with 50 ng/ml LONO-Q ($6.1\pm2.5$% G2/M for control, and $18.4\pm2.5$*% for G2/M of LONO-Q, n=3, *$p<0.05$ vs. control 10% FBS) (FIG. 6). This result correlates to the CFDA assay pattern obtained by flow cytometry in serum deprivation conditions.

Example 5

Detection of Intracellular Reactive Oxygen and Nitrogen Species (ROS)

Materials and Methods:

The detection of reactive species was performed by the ROS Detection Kit (Enzo Life Sciences, Plymouth Meeting, Pa.) according to the manufacturer's instructions. This assay allows detecting ROS production in living cells by flow cytometry. The dye detection reagent reacts with hydrogen peroxide, peroxynitrite and hydroxyl radicals. FN1 cells at a density of $10^6$/ml were plated and cultured in 6-well plates for 24 hours in incubator containing 5% $CO_2$ at $37°$ C. After 12 hours of treatment in the absence (control) or presence of 50 ng/ml LONO-Q in culture medium containing 1% or 10% FBS, cells were washed twice with washing buffer and then incubated with the ROS detection solution for 30 minutes at $37°$ C. and protected from light. Then, the cells were washed with wash buffer supplied by the manufacturer and centrifuged at 1500 rpm for 10 minutes. The supernatant was discarded and the cell button resuspended in 200 µl of PBS. The fluorescence was determined at $\lambda=485$ nm for excitation and emission $\lambda=590$ nm for a FACScalibur™ flow cytometry system using CellQuest™ software with the acquisition of 10,000 events having as parameters FSC (size) and SSC (granularity/complexity) linear scale and FL1/FL2 on logarithmic scales. The results were expressed as the mean±SEM (standard error of the mean) of 3 independent experiments.

Figure 7:
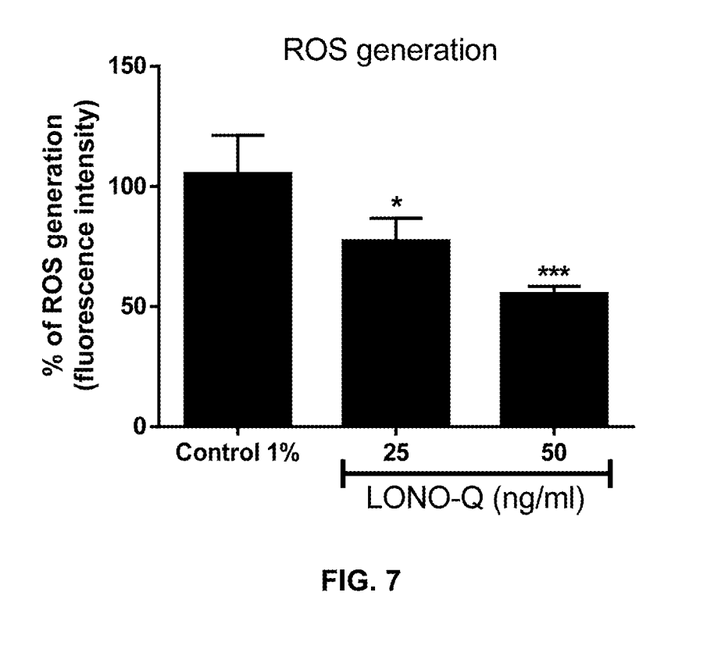
FIG. 7 is a bar graph showing the detection assay of intracellular reactive oxygen and nitrogen species (ROS) of cells treated with LONO-Q peptide for 48 hours in the presence of 1% FBS.
Figure 8:
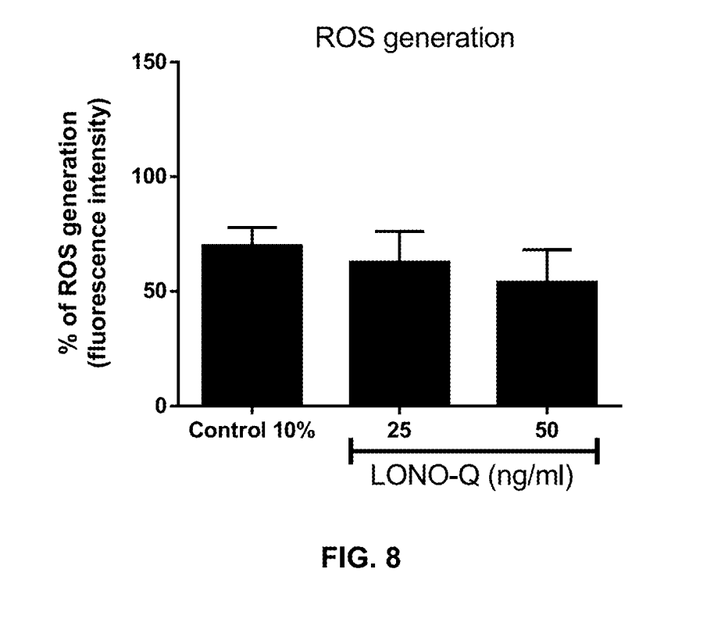
FIG. 8 is a bar graph showing the detection assay of intracellular reactive oxygen and nitrogen species (ROS) of cells treated with LONO-Q peptide for 48 hours in the presence of 10% FBS.

Results:

It was well documented in the literature that serum deprivation is able to induce in vitro mitochondrial dysfunctions including loss of mitochondrial membrane potential and ROS generation. We used the fluorescent cationic dye Rh123 as an indicator of the energy state of the mitochondria (Benel, L., et al., *Mitochondrial uptake of rhodamine 123 by rabbit articular chondrocytes*. Cytometry, 1986. 7(3): p. 281-5). Serum-deprived cultures (1% FBS) treated with LONO-Q (FIG. 7) showed a statistically significant decrease of ROS production with 25 and 50 ng/ml LONO-Q (Student's t test, * $p<0:05$ and *** $p<0.001$ versus control 1% FBS). Next, we examined the effect of LONO-Q in normal cell growth (10% FBS). A shown in FIG. 8, there was no statistically significant decrease in ROS generation. These findings indicate that LONO-Q treatment strongly induced protection against damage wherein cells have been subjected to stressing conditions of serum deprivation.

Example 6

Ultrastructure of Fibroblasts by Transmission Electron Microscopy (TEM)

Materials and Methods:

Severe morphological changes in normal fibroblasts are observed after serum deprivation conditions consistent with those of apoptotic cell death. In order to investigate the effect of LONO-Q on morphological changes induced by prolonged serum deprivation, FN1 cell cultures were prepared for transmission electron microscopy (TEM). TEM provides ultra-structural evidence about the nature of cell death (Kulkarni, G. V. and C. A. McCulloch, *Serum deprivation induces apoptotic cell death in a subset of Balb/c 3T3 fibroblasts*. J Cell Sci, 1994. 107 (Pt 5): p. 1169-79).

Human fibroblasts were treated with the peptide LONO-Q for 48 hours in the presence of 1% or 10% FBS. Cells were washed 3 times with PBS and gently collected in a tube with the help of a cell scraper. The cell suspension was centrifuged, and the cell button re-suspended in a solution of 3% glutaraldehyde and 2% paraformaldehyde diluted in sodium cacodylate. The cell button was post-fixed in 1% solution of osmium tetroxide for 1 hour, washed with PBS and distilled water and dehydrated in a graded ethanol series (30, 60, 70, 80 and 100%). Finally, the epoxy resin was mixed with warm ethanol (1:1) for infiltration, and only the resin was used for the incorporation of cells (60° C./48 h). Ultrathin sections (50 nm) were cut with an ultramicrotome (Leica Ultracut™ UCT) and stained with 5% uranyl acetate in 50% ethanol and 2% aqueous solution of citrate. The obtained sections were photographed using a TEM (LEO™ 906E, Zeiss, Japan) at an accelerating voltage of 80 kV.

Figure 9:
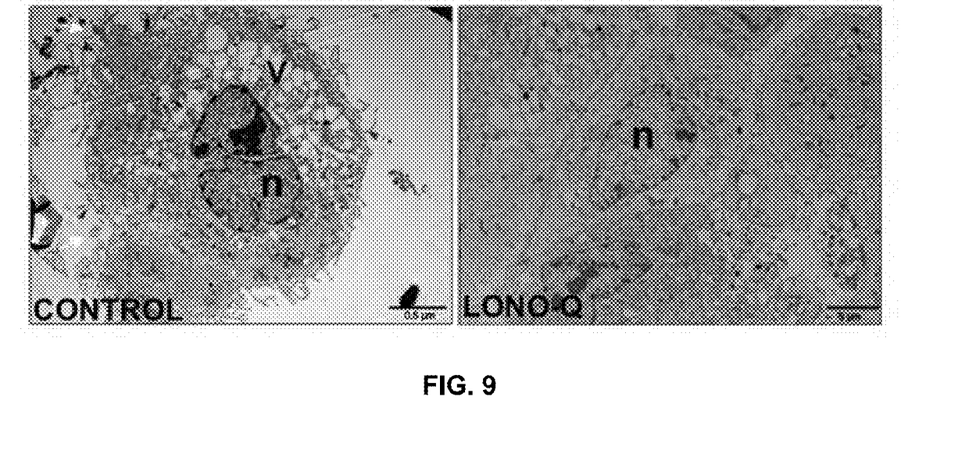
FIG. 9 is a transmission electron microscopy (TEM) photograph of FN1 fibroblasts incubated during 48 hours in the absence (control) or in the presence of 50 ng/ml LONO-Q peptide in RPMI containing 1% FBS. Scale bars: 0.5 μm (control) and 5 μm (LONO-Q). N, nucleus; V, vacuoles. White arrows indicate apoptotic bodies.
Figure 10:
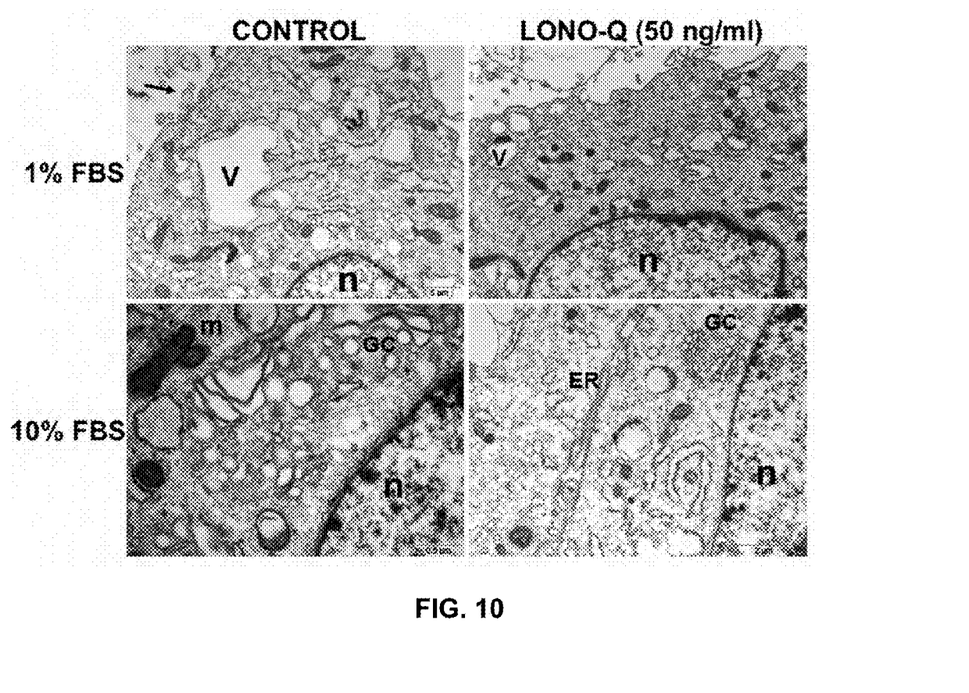
FIG. 10 is a transmission electron microscopy (TEM) photograph of FN1 fibroblasts incubated during 48 hours in the absence (control) or in the presence of 50 ng/ml LONO-Q peptide in RPMI containing 1% or 10% of FBS. Scale bars: 5 μm (1% FBS: control and LONO-Q), 2 μm (LONO-Q in 10% FBS) and 0.5 μm (control 10% FBS). N, nucleus; V, vacuole, GC, Golgi complex; ER, endoplasmic reticulum; m, mitochondria. Black arrow in 1% FBS control indicates apoptotic bodies.

Results:

As shown in FIG. 9, serum-deprived cells have lost the oval appearance and filopodia, and show typical features of apoptosis, including a number of membrane-bound apoptotic bodies, condensation of nuclear chromatin and nuclear fragmentation. Serum-deprived cells also become highly vacuolated (FIGS. 9 and 10), as observed in other cellular types after prolonged serum-starvation conditions. In contrast, treatment of starving cells with LONO-Q retards most of the effects observed in serum deprived cells. Some apoptotic characteristics such as appearance of apoptotic bodies and loss of extracellular matrix organization were reduced (FIG. 9). As well, cytoplasm, nucleus and organelles with normal morphology were seen (FIG. 10).

Example 7

Analysis of Extracellular Matrix Molecules by Fluorescence Microscopy

Materials and Methods:

Previous studies have reported the importance of extracellular matrix components for maintaining cell survival of serum-deprived cells and that survival is enhanced by cell-cell contact. To confirm the synthesis of extracellular matrix molecules, fibroblast cultures were marked with antibodies specific for laminin and fibronectin following treatment with the synthetic peptide.

The cells were cultured in 24-well plates containing sterile coverslips for 72 hours in the presence or absence (control) of peptide LONO-Q (50 ng/ml) in DMEM medium supplemented with 10% FBS. After treatment, the medium was removed and cells were washed with PBS and fixed with 3.7% paraformaldehyde for 10 minutes. Triton X-100 (0.1%) was added for 15 minutes for permeabilization of the plasma membrane, followed by addition of the primary antibody and incubation for 12 hours (overnight) in the dark at 4° C. The cells were washed with PBS, the secondary antibody was added and the cells were kept for 1 hour at room temperature in the dark. Antibodies were diluted according to the manufacturer's recommendation. After washing, the endothelial cell nuclei were stained with 4',6-diamidino-2-phenylindole (DAPI) reagent (Invitrogen) and slides were mounted on coverslips containing 4 µl of antifade solution (Vectashield™, Vector-H1000, that serves to preserve fluorescence). Cells were viewed with an Axio™ Imager A1 fluorescence microscope (Carl Zeiss, Germany).

Antibody Dilution

Primary antibodies in blocking buffer: 10% FBS, 1% BSA in TBS (0.1% Triton X-100 in PBS):

Mouse monoclonal to Collagen type I [Col-I] (abcam): 1/1000

Rabbit polyclonal to Fibronectin (abcam): 2 µg/ml

Rabbit polyclonal to Laminin alpha 4 (abcam): 1/500

Mouse monoclonal [VN58-1] Vitronectin (ab13413): 5 µg/ml Secondary antibody in 1% bovine serum albumin (BSA) in PBS:

Alexa Fluor™ 568 goat anti-rabbit IgG (Life Technologies): 10 µg/ml

Alexa Fluor™ 4888 goat anti-mouse IgG (Life Technologies): 10 µg/ml

Figure 11:
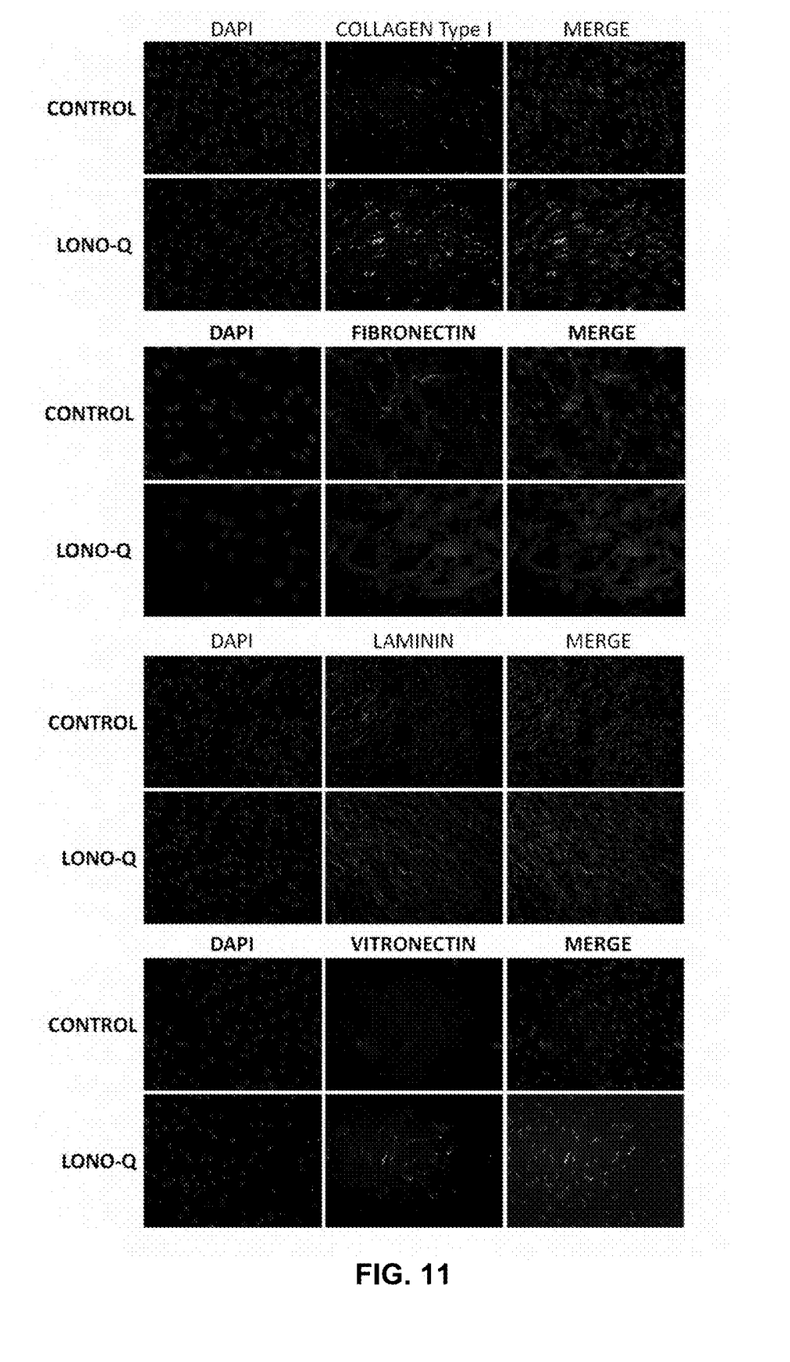
FIG. 11 shows fluorescence microscopy photographs showing the effect of LONO-Q peptide (50 ng/ml) on the expression of extracellular matrix (ECM) molecules after 72 hours of treatment in DMEM medium containing 10% FBS.
Figure 12:
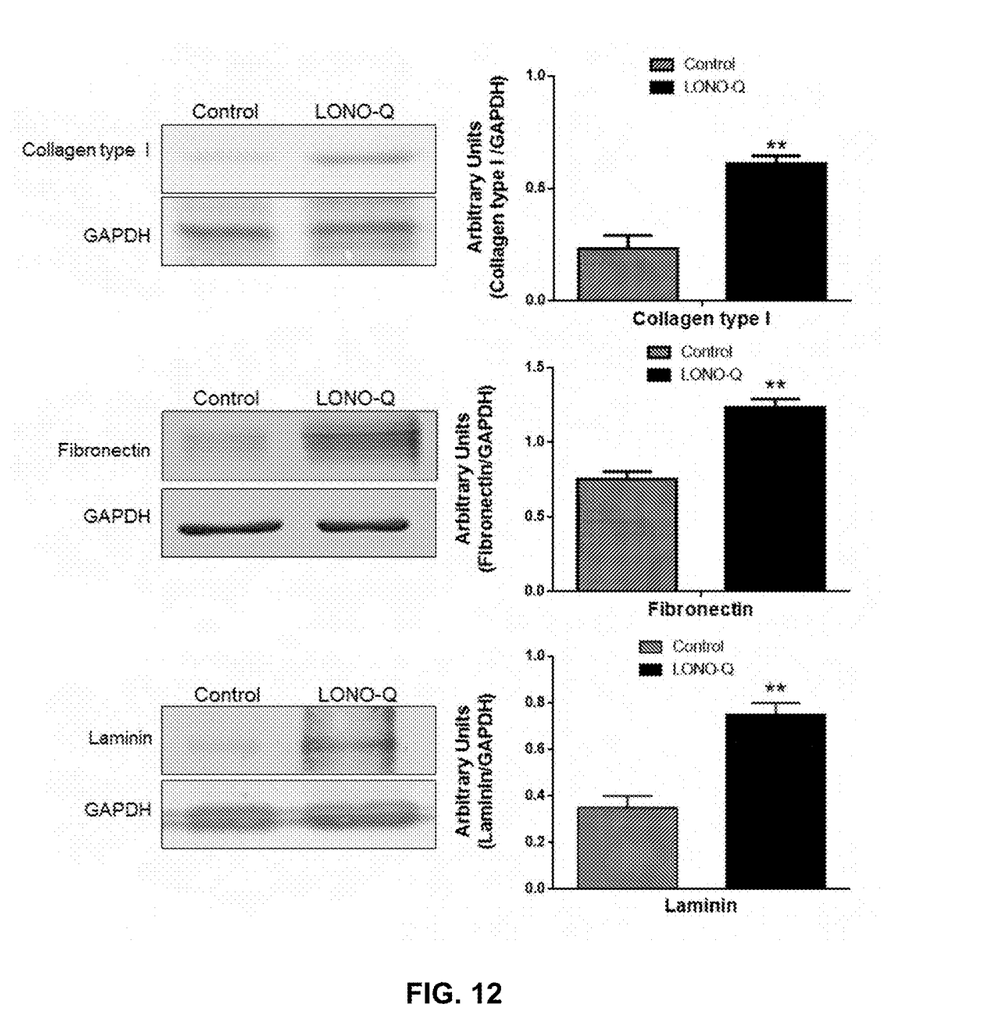
FIG. 12 is the quantitative analysis by Western blot of the expression of ECM molecules induced by the LONO-Q peptide (50 ng/ml) in FN1 fibroblasts treated during 72 hours in DMEM containing 10% FBS. The bands were analyzed by densitometry. The figures indicate the mean of 3 independent experiments ±SEM (standard error of the mean).

Results:

FN1 cells treated for 48 h with 50 ng/ml LONO-Q produced increased amounts of extracellular matrix components including collagen I, fibronectin, laminin and vitronectin (FIG. 11).

Example 8

Analysis of Extracellular Matrix Molecules by Western Blot

Materials and Methods:

Fibroblasts were grown in 25 cm$^2$ bottles for 72 hours in the presence or absence (negative control) of 50 ng/ml LONO-Q in DMEM medium supplemented with 10% FBS. After treatment, the medium was removed and cells were washed with PBS. Cells were detached after addition of 300 µl of radioimmunoprecipitation assay (RIPA) buffer (50 mM Tris-HCl, pH 7.4, 1 mM EDTA, 0.5% Nonidet, 1 mM MgCl$_2$, 10% glycerol, 100 mM NaCl). The cell extract was kept on ice for 30 minutes. Protein concentration was quantified by the Bradford method (Bradford, M. M., *A rapid and sensitive method for the quantitation of microgram quantities of protein utilizing the principle of protein-dye binding*. Anal Biochem, 1976. 72: p. 248-54) and the samples stored at −80° C. prior to use.

The cell lysate (containing the same amount of protein) was analyzed by SDS-PAGE 10% (w/v) (Laemmli, U. K., *Cleavage of structural proteins during the assembly of the head of bacteriophage T4*. Nature, 1970. 227(5259): p. 680-5) under reducing conditions by mixing (1:1) with sample buffer without dye (Tris-HCl 0.5 M, pH 6.8, containing 10% SDS, 20% glycerol (v/v), 2% β-mercaptoethanol). After electrophoresis, the gel and polyvinylidene difluoride (PVDF) membrane (Millipore) were treated with transfer buffer before the preparation of the vertical module (miniVE™ System Blot Module, GE Healthcare) filled with transfer buffer (25 mM Tris-HCl, pH 8.4, 192 mM glycine and 15% methanol). The transfer was carried out in the cold (4° C.) in a current of 80 mA for 16 hours. After transfer, the PVDF membrane was treated with specific primary antibodies dissolved in blocking solution (5% skim milk in TBS-T buffer) according to the manufacturer's recommendations.

Primary antibodies used include:

Mouse monoclonal to Collagen type I [Col-I] (Abcam): 1/200

Rabbit polyclonal to Fibronectin (Abcam): 1/200

Rabbit polyclonal to Laminin alpha 4 (Abcam): 1/200

We also used the rabbit polyclonal antibody to GAPDH (Santa Cruz), which recognizes the constitutive GAPDH protein.

The secondary antibody used was an anti-rabbit or mouse IgG1 coupled to horseradish peroxidase (HRP) (KPL) (1:1000). The developer was the ECL kit, which detects peroxidase substrate.

The bands were visualized in a MiniBIS™ Pro imaging system (DNR Bio-Imaging Systems) using the program GelCapture™ Version 4:24 (DNR Bio-Imaging Systems) Statistical analyses were carried out with the program Gel-Quant™ Version 2.7.0 (DNR Bio-Imaging Systems). The density of the bands was compared with the protein band for constitutive GAPDH, used to normalize the concentration of the cell extracts. Data were expressed as arbitrary units.

Statistical analysis was performed by the method of variance (ANOVA) with multiple comparison test of Tukey-Kramer and Student's t test. Values were expressed as mean±standard deviation for each experiment. Values were considered significant when $p<0.05$ (*), $p<0.01$ () or $p<0.001$ (*).

The embodiments described herein are intended to be illustrative of the present compositions and methods and are not intended to limit the scope of the present invention. Various modifications and changes consistent with the description as a whole and which are readily apparent to the person of skill in the art are intended to be included. The appended claims should not be limited by the specific embodiments set forth in the examples, but should be given the broadest interpretation consistent with the description as a whole.

7. The method according to claim 4 wherein the peptide stimulates the synthesis of DNA by promoting the S phase of the cell cycle.

8. The method according to claim 4 wherein the peptide stimulates the production of at least one extracellular matrix (ECM) protein.

9. The method according to claim 8 wherein the at least one ECM protein is one or more proteins selected from collagen, fibronectin, laminin, and vitronectin.

10. The method according to claim 4 wherein the peptide reduces the production of reactive oxygen species (ROS).

11. The method according to claim 4 wherein the peptide reduces apoptosis.

12. The method according to claim 4 wherein the peptide reduces damage to cell morphology and/or integrity under stress conditions of serum deprivation.

13. A method of treating a condition associated with insufficient proliferation or survival of cells in a subject in need thereof, the method comprising administering a peptide according to claim 1, or a pharmaceutical composition thereof, to the subject.

14. The method according to claim 13 wherein the subject is a human patient.

The invention claimed is:

1. A peptide consisting of the amino acid sequence DYFKDGKDVN (SEQ ID NO: 2).

2. A pharmaceutical composition comprising the peptide according to claim 1 and one or more pharmaceutically acceptable carriers.

3. A cosmetic composition comprising the peptide according to claim 1 and one or more cosmetically acceptable carriers.

4. A method of stimulating proliferation or survival of a cell, the method comprising exposing the cell to the peptide according to claim 1.

5. The method according to claim 4 wherein the cell is an endothelial cell or fibroblast.

6. The method according to claim 5 wherein the fibroblast is a dermal fibroblast.

15. The method according to claim 13 wherein the condition is associated with insufficient production of at least one extracellular matrix (ECM) protein.

16. The method according to claim 15 wherein the at least one ECM protein is one or more proteins selected from collagen, fibronectin, laminin, and vitronectin.

17. The method according to claim 13 wherein the condition is associated with production of reactive oxygen species.

18. The method according to claim 13 wherein the condition is associated with apoptosis.

19. The method according to claim 13 wherein the condition is associated with tissue degeneration.

* * * * *